United States Patent
Herold et al.

(10) Patent No.: US 8,071,773 B2
(45) Date of Patent: Dec. 6, 2011

(54) HETEROCYCLIC SPIRO-COMPOUNDS AS ALDOSTERONE SYNTHASE INHIBITORS

(75) Inventors: Peter Herold, Basel (CH); Robert Mah, Muttenz (CH); Vincenzo Tschinke, Binningen (CH); Aleksandar Stojanovic, Basel (CH); Christiane Marti, Rheinfelden (CH); Nathalie Jotterand, Basel (CH); Christoph Schumacher, Bettingen (CH); Michael Quirmbach, Basel (CH)

(73) Assignee: NovartisAG, Basel (CH)

( * ) Notice: Subject to any disclaimer, the term of this patent is extended or adjusted under 35 U.S.C. 154(b) by 972 days.

(21) Appl. No.: 11/921,312

(22) PCT Filed: May 30, 2006

(86) PCT No.: PCT/EP2006/062696
§ 371 (c)(1),
(2), (4) Date: Nov. 30, 2007

(87) PCT Pub. No.: WO2006/128853
PCT Pub. Date: Dec. 7, 2006

(65) Prior Publication Data
US 2009/0111840 A1    Apr. 30, 2009

(30) Foreign Application Priority Data
May 31, 2005  (CH) .................................. 00923/05

(51) Int. Cl.
*C07D 471/20*  (2006.01)
*A61K 31/438*  (2006.01)
*A61K 31/437*  (2006.01)

(52) U.S. Cl. ......................................... 546/18; 514/278
(58) Field of Classification Search .................... 546/18; 514/278
See application file for complete search history.

(56) References Cited

FOREIGN PATENT DOCUMENTS

| WO | 01/76574 | 10/2001 |
|---|---|---|
| WO | 2004/014914 | 2/2004 |
| WO | 2004/046145 | 6/2004 |

OTHER PUBLICATIONS

Online: "Calculating the Degrees of Unsaturation From a Compound's Molecular Formula" from Organic Chemistry handouts Department of Chemistry Manhattanville College "http://faculty.mville.edu/ParikhS/courses/chm2001/docs/Handouts/Degree%20of%20unsaturation.pdf" accessed Nov. 20, 2010.*

Browne et. al. "Fadrozole Hydrochloride: A Potent, Selective, Nonsteroidal Inhibitor of Aromatase for the Treatment of Estrogen-Dependent Disease" Journal of Medicinal Chemistry 1991, 34, 725-736.*

Ulmschneider et. al. "Synthesis and Evaluation of (Pyridylmethylene)tetrahydronaphthalenes/-indanes and Structurally Modified Derivatives: Potent and Selective Inhibitors of Aldosterone Synthase" Journal of Medicinal Chemistry 2005, 48, 1563-1575.*

Ulmschneider et. al. "Synthesis and Evaluation of Imidazolylmethylenetetrahydronaphthalenes and Imidazolylmethyleneindanes: Potent Inhibitors of Aldosterone Synthase" Journal of Medicinal Chemistry 2005, 1796-1805.*

International Search Report issued Aug. 10, 2006 in the International (PCT) Application PCT/EP2006/062696 of which the present application is the U.S. National Stage.

* cited by examiner

*Primary Examiner* — David K O Dell
(74) *Attorney, Agent, or Firm* — Wenderoth, Lind & Ponack, L.L.P.

(57) ABSTRACT

The patent application relates to new heterocyclic compounds of the general formula (I) in which R, $R^1$, $R^2$, W, X, Y, Z and n have the definitions elucidated in more detail in the description, to a process for preparing them and to the use of these compounds as medicaments, particularly as aldosterone synthase inhibitors.

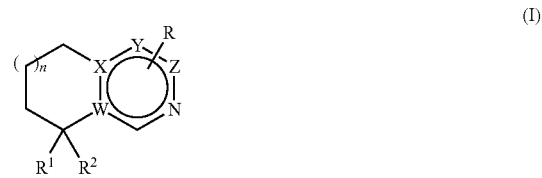

6 Claims, No Drawings

HETEROCYCLIC SPIRO-COMPOUNDS AS ALDOSTERONE SYNTHASE INHIBITORS

FIELD OF THE INVENTION

The invention relates to new heterocycles, to processes for preparing the compounds according to the invention, to pharmaceutical products comprising them, and to their use as active pharmaceutical ingredients, in particular as aldosterone synthase inhibitors.

DETAILED DESCRIPTION OF THE INVENTION

The present invention first provides compounds of the general formula

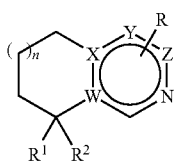

in which
W is C or, if Z is a bond and X is C, W is alternatively N;
X is C or, if Z is a bond, X is alternatively N;
Y is C or, if Z is C, Y is alternatively N;
Z is C or a bond;
the ring containing Y being maximum unsaturated;
R is hydrogen, $C_1$-$C_8$-alkyl, $C_1$-$C_8$-alkoxy-$C_0$-$C_4$-alkyl, halogen, tri-$C_1$-$C_4$-alkylsilyl, deuterium or trifluoromethyl;
$R^1$ together with $R^2$ is a 5-14-membered carbocyclic or heterocyclic ring, which rings may be substituted by 14 $C_1$-$C_8$-alkyl, $C_0$-$C_8$-alkylcarbonyl, halogen, cyano-$C_0$-$C_6$-alkyl, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl, heterocyclyl, arylcarbonyl or heterocyclylcarbonyl, it being possible for aryl and heterocyclyl to be unsubstituted or substituted by 1-4 $C_1$-$C_8$-alkyl, $C_0$-$C_8$-alkylcarbonyl, halogen, cyano-$C_0$-$C_6$-alkyl, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy or $C_1$-$C_8$-alkoxycarbonyl;
n is a number 0, 1 or 2;
and their salts, preferably their pharmaceutically useful salts.

The aryl term stands for an aromatic hydrocarbon which contains generally 5-14, preferably 6-10, carbon atoms and is for example phenyl, or naphthyl, e.g. 1- or 2-naphthyl. Preference is given to aryl having 6-10 carbon atoms, particularly phenyl or 1- or 2-naphthyl. The stated radicals may be unsubstituted or may be substituted one or more times, such as once or twice, in which case the substituent may be in any position, such as in the o, m or p position of the phenyl radical or in the 3 or 4 position of the 1- or 2-naphthyl radical, and there may also be two or more identical or different substituents.

A 5-14-membered carbocyclic ring (carbocyclyl) is a saturated or unsaturated, 5-8-membered, more preferably 6-membered, monocyclic ring system, a saturated or unsaturated, 9-11-membered, more preferably 10-membered, bicyclic ring system and also a saturated or unsaturated, 7-14-membered tricyclic ring system. The stated radicals may be unsubstituted or may be substituted one or more times, such as once or twice, and there may also be two or more identical or different substituents.

A saturated, monocyclic, carbocyclic, 4-8-membered ring is for example cyclohexyl.

A saturated, bicyclic, carbocyclic, 9-11-membered ring is for example decalinyl.

The heterocyclyl term stands for a saturated or unsaturated, 4-8-membered, more preferably 5-membered, monocyclic ring system, for a saturated or unsaturated, 7-12-membered, more preferably 9-10-membered, bicyclic ring system and also for a saturated or unsaturated, 7-12-membered tricyclic ring system, in each case containing an N, O or S atom in at least one ring, it also being possible for an additional N, O or S atom to be present in one ring, and the heteroatoms being separated preferably by at least one carbon atom. The stated radicals may be unsubstituted or may be substituted one or more times, such as once or twice, and there may also be two or more identical or different substituents.

Unsaturated monocyclic heterocyclyl-$C_0$-$C_4$-alkyl is for example pyrrolyl, thiophenyl, thiazolyl or oxazolyl.

Saturated monocyclic heterocyclyl-$C_0$-$C_4$-alkyl is for example pyrrolidinyl or pyranyl.

Unsaturated bicyclic heterocyclyl-$C_0$-$C_4$-alkyl is for example 4,5,6,7-tetrahydroisobenzo-furanyl, 4,5,6,7-tetrahydrobenzothiazolyl, benzofuranyl, benzothiophenyl, isoquinolyl or quinolyl.

$C_1$-$C_8$-Alkyl can be linear- or branched and/or bridged and is for example methyl, ethyl, propyl, isopropyl, butyl, isobutyl, secondary-butyl, tertiary-butyl, or a pentyl, hexyl or heptyl group.

$C_1$-$C_8$-Alkoxy is for example $C_1$-$C_5$-alkoxy, such as methoxy, ethoxy, propyloxy, isopropyloxy, butyloxy, isobutyloxy, secondary-butyloxy, tertiary-butyloxy or pentyloxy, but can also be a hexyloxy or heptyloxy group.

$C_1$-$C_8$-Alkoxy-$C_0$-$C_4$-alkyl is for example, in addition to the definitions stated for $C_1$-$C_8$-alkoxy, $C_1$-$C_5$-alkoxy-$C_1$-$C_4$-alkyl, such as methoxyethyl, ethoxyethyl, propyloxymethyl, isopropyloxy-butyl, butyloxymethyl, isobutyloxyethyl, secondary-butyloxypropyl, tertiary-butyloxybutyl or pentyloxymethyl, but can also be a hexyloxymethyl or heptyloxymethyl group.

$C_1$-$C_8$-Alkoxycarbonyl is preferably $C_1$-$C_5$-alkoxycarbonyl, such as methoxycarbonyl, ethoxy-carbonyl, propyloxycarbonyl, isopropyloxycarbonyl, butyloxycarbonyl, isobutyloxycarbonyl, secondary-butyloxycarbonyl or tertiary-butyloxycarbonyl.

$C_0$-$C_8$-Alkylcarbonyl is for example formyl, acetyl, propionyl, propylcarbonyl, isopropyl-carbonyl, butylcarbonyl, isobutylcarbonyl, secondary-butylcarbonyl or tertiary-butylcarbonyl.

Cyano-$C_0$-$C_6$alkyl may derive from linear or branched and/or bridged alkyl and is for example cyano, cyanomethyl, 2-cyanoethyl, 3-cyanopropyl, 2-cyanoisopropyl, 4-cyanobutyl, 2-cyano-tertiary-butyl, or a cyanopentyl or cyanohexyl group.

$C_0$-$C_8$-Alkylcarbonyl is for example formyl, acetyl, propionyl, propylcarbonyl, isopropyl-carbonyl, butylcarbonyl, isobutylcarbonyl, secondary-butylcarbonyl or tertiary-butylcarbonyl.

Carboxy-$C_1$-$C_4$-alkyl is for example carboxymethyl, 2-carboxyethyl, 2- or 3-carboxypropyl, 2-carboxy-2-methylpropyl, 2-carboxy-2-ethylbutyl or 4-carboxybutyl, especially carboxymethyl.

Mono- or di-$C_1$-$C_8$-alkylaminocarbonyl is for example $C_1$-$C_4$-alkylaminocarbonyl, such as methylaminocarbonyl, ethylaminocarbonyl, propylaminocarbonyl or butylaminocarbonyl, or di-$C_1$-$C_4$-alkylaminocarbonyl, such as dimethylaminocarbonyl, N-methyl-N-ethylamino-carbonyl, diethylaminocarbonyl, N-methyl-N-propylaminocarbonyl or N-butyl-N-methyl-aminocarbonyl.

$C_0$-$C_8$-Alkylcarbonylamino is for example formylamino, acetylamino, propionylamino, propylcarbonylamino, isopropylcarbonylamino, butylcarbonylamino, isobutylcarbonylamino, secondary-butylcarbonylamino or tertiary-butylcarbonylamino.

$C_0$-$C_8$-Alkylcarbonyl-$C_1$-$C_8$-alkylamino is for example formyl-, acetyl-, propionyl-, propylcarbonyl-, isopropylcarbonyl-, butylcarbonyl-, isobutylcarbonyl-, secondary-butylcarbonyl- or tertiary-butylcarbonyl-methylamino, formyl-, acetyl-, propionyl-, propylcarbonyl-, isopropylcarbonyl-, butylcarbonyl-, isobutylcarbonyl-, secondary-butylcarbonyl- or tertiary-butylcarbonyl-ethylamino, formyl-, acetyl-, propionyl-, propylcarbonyl-, isopropylcarbonyl-, butylcarbonyl-, isobutylcarbonyl-, secondary-butylcarbonyl- or tertiary-butylcarbonyl-propylamino or formyl-, acetyl-, propionyl-, propylcarbonyl-, isopropylcarbonyl-, butylcarbonyl-, isobutylcarbonyl-, secondary-butylcarbonyl- or tertiary-butylcarbonyl-butylamino.

Halogen is for example fluoro, chloro, bromo or iodo.

The groups of compounds specified below should not be considered as being closed; on the contrary, parts of these groups of compounds may be replaced by one another or by the definitions given above, or may be omitted, in a meaningful way, such as in order to replace more general definitions by more specific definitions.

Preferred compounds of the formula (I) are compounds of the general formulae

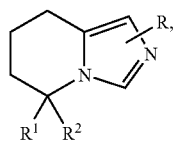

(Ia)

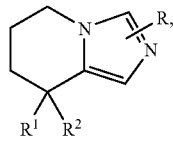

(Ib)

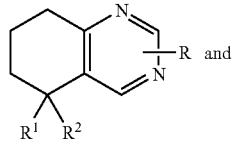

(Ic)

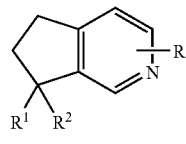

(Id)

the definitions of the substituents R, $R^1$ and $R^2$ being as specified for compounds of the formula (I).

R is very preferably hydrogen or deuterium.

$R^1$ is together with $R^2$ preferably monocyclic $C_5$-$C_7$-carbocyclyl, bicyclic $C_9$-$C_{11}$-carbocyclyl, pyrrolidinyl or pyranyl, which radicals may be substituted by 14 oxo, cyano-$C_0$-$C_6$-alkyl, $C_0$-$C_8$-alkylcarbonyl, heterocyclyl or heterocyclylcarbonyl, it being possible for heterocyclyl to be substituted by $C_1$-$C_8$-alkyl, halogen, cyano or $C_0$-$C_8$-alkylcarbonyl.

n is preferably a number 0 or 1.

Very particular preference is therefore given for example to compounds of the general formulae (I), (Ia), (Ib), (Ic) and (Id) in which R is hydrogen or deuterium; and $R^1$ together with $R^2$ is cyclohexyl, decalinyl, pyrrolidinyl or pyranyl, which radicals may be substituted by 14 oxo, cyano-$C_0$-$C_6$-alkyl, $C_0$-$C_8$-alkylcarbonyl, heterocyclyl or heterocyclylcarbonyl, it being possible for heterocyclyl to be substituted by $C_1$-$C_8$-alkyl, halogen, cyano or $C_0$-$C_8$-alkylcarbonyl.

Particularly preferred compounds of the formula (I) are those of the general formulae (Ia'-Id')

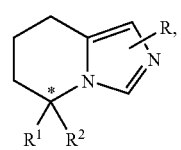

(Ia')

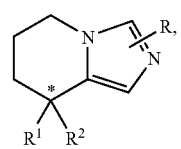

(Ib')

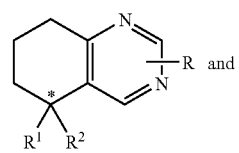

(Ic')

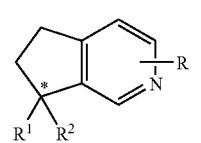

(Id')

the definitions of the substituents R, $R^1$ and $R^2$, $R^3$ being as specified for the compounds of the formula (I).

"*" denotes an asymmetric carbon atom.

The compounds of the formula (I) which possess at least one asymmetric carbon atom can exist in the form of optically pure enantiomers, mixtures of enantiomers, or racemates. Compounds having a second asymmetric carbon atom can exist in the form of optically pure diastereomers, mixtures of diastereomers, diastereomeric racemates, mixtures of diastereomeric racemates, or mesocompounds. The invention embraces all of these forms. Mixtures of enantiomers, racemates, mixtures of diastereomers, diastereomeric racemates, or mixtures of diastereomeric racemates can be fractionated by conventional methods, such as by racemate resolution, column chromatography, thin-layer chromatography, HPLC and the like.

The compounds of the formula (Ia'-Id') have at least one asymmetric carbon atom, which is labelled "*". The compounds mentioned are to be understood as a single compound having a specific configuration around the designated asymmetric carbon atom. If a synthesis method is used which leads to racemic compounds, the racemate resolution is carried out in accordance with conventional methods, such as via a chiral HPLC column. Compounds of the formula (Ia'-Id') as described in the present invention exhibit a pronounced aldosterone synthase and/or 11-β-hydroxylase inhibitory activity. The aforementioned activity can, as the skilled worker is well aware and as described below, be comfortably determined via cellular assays based on the NCI-H295R human adrenocortical carcinoma cell line. In the above-mentioned assay system, compounds of the formula (Ia'-Id') have an activity which is at least 20 times better, but preferably 40 times better, than the substances of the formula (Ia'-Id') with the opposite configuration around the asymmetric carbon atom labelled "*".

The expression "pharmaceutically useful salts" embraces salts with organic or inorganic acids, such as hydrochloric acid, hydrobromic acid, nitric acid, sulphuric acid, phosphoric acid, citric acid, formic acid, maleic acid, acetic acid, succinic acid, tartaric acid, methane-sulphonic acid, p-toluenesulphonic acid and the like. Salts of compounds containing salt-forming groups are, in particular, acid addition salts, salts with bases or else, if appropriate, if two or more salt-forming groups are present, are mixed salts or inner salts.

The compounds of the formula (I) can be prepared analogously to preparation processes known from the literature. Details of the specific preparation variants can be found from the examples.

The compounds of the formula (I) can also be prepared in optically pure form. Separation into antipodes is possible by methods known per se, either, preferably, at an early stage in synthesis, by salt formation with an optically active acid such as, for example, (+)- or (−)-mandelic acid and separation of the diastereomeric salts by fractional crystallization, or, preferably, at a fairly late stage, by derivatization with a chiral auxiliary component, such as, for example, (+)- or (−)-camphanyl chloride and separation of the diastereomeric products by chromatography and/or crystallization and subsequent cleavage of the bond to the chiral auxiliary. The pure diastereomeric salts and derivatives can be analysed to determine the absolute configuration of the compound present, using customary spectroscopic methods, with single-crystal X-ray spectroscopy representing one particularly appropriate method.

Salts are primarily the pharmaceutically useful or non-toxic salts of compounds of the formula (I). Such salts are formed for example by compounds of the formula (I) containing an acidic group, such as a carboxyl or sulpho group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxy-lower alkyl) amines, such as ethanolamine, diethanolamine or triethanolamine, tris(hydroxymethyl)methylamine or 2-hydroxy-tertiary-butylamine, N,N-di-lower alkyl-N-(hydroxy-lower alkyl)amine, such as N,N-di-N-dimethyl-N-(2-hydroxyethyl)amine, or N-methyl-D-glucamine, or quaternary ammonium hydroxides, such as tetrabutylammonium hydroxide. The compounds of the formula (I) containing a basic group, such as amino group, can form acid addition salts, with suitable inorganic acids for example, such as hydrohalic acid, such as hydrochloric acid, hydrobromic acid, or sulphuric acid with replacement of one or both protons, phosphoric add with replacement of one or more protons, orthophosphoric acid or metaphosphoric acid for example, or pyrophosphoric add with replacement of one or more protons, or with organic carboxylic, sulphonic or phosphonic acids or N-substituted sulphamic acids, examples being acetic acid, propionic add, glycolic acid, succinic acid, maleic acid, hydroxymaleic acid, methylmaleic acid, fumaric add, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, such as α-amino acids, and also methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates), or with other acidic organic compounds, such as ascorbic acid. Compounds of the formula (I) containing acidic and basic groups can also form inner salts.

Isolation and purification can also be carried out using pharmaceutically unsuitable salts.

The compounds of the formula (I) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl)-alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the dose relationship between a free compound, a prodrug derivative and a salt compound, a defined compound in this invention also includes its prodrug derivative and salt form, insofar as this is possible and appropriate.

Aldosterone is a steroidal hormone which is synthesized in the zona glomerulosa cells of the adrenal cortex by the enzyme aldosterone synthase (CYP11B2). Aldosterone production and secretion is regulated by the adrenocorticotropic hormone (ACTH), angiotensin 11, potassium and sodium ions. The primary biological function of aldosterone is the regulation of the salt balance, with aldosterone controlling the reabsorption of sodium ions from the renal filtrate and the secretion of potassium ions into the renal filtrate. The state of excessive aldosterone secretion, also called hyperaldosteronism, can lead to high blood pressure, hypokalaemia, alkalosis, muscle weakness, polyuria, polydipsia, edemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The compounds described can be employed for preventing, delaying the progression of or treating states such as hypokalaemia, hypertension, congestive heart failure, acute and—in particular—chronic renal failure, cardiovascular restenosis, atherosclerosis, metabolic syndrome (syndrome X), adiposity (obesity), vasculitis, primary and secondary hyperaldosteronism, proteinuria, nephropathy, diabetic complications, such as diabetic nephropathy, myocardial infarction, coronary heart disease, increased collagen formation, fibrosis, vascular and coronary tissue changes (remodelling) secondary to high blood pressure, endothelial dysfunction, and oedemas secondary to sclerosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is regulated by ACTH. The primary biological function of cortisol is to regulate the production and the provision of carbohydrates for the brain and other metabolically active tissues. Increased cortisol production and secretion is a normal physiological response to stress and leads to the essential mobilization of fats, proteins and carbohydrates to cover increased physical energy demand. Chronically excessive cortisol release describes the condition of Cushing's syndrome. Cushing's syndrome may come about on the one hand as a result of cortisol hypersynthesis, which may be generated by an adrenocortical tumour, or on the other hand as the consequence of excessive stimulation of the adrenal cortex by ACTH. The first form is referred to as primary hypercortisolism, the second form as secondary hypercortisolism. An excessive and persistent cortisol secretion may also accompany a stress response, which can lead to depression, hyperglycaemia and the suppression of the immune system.

The chemical compounds described in this invention inhibit the enzyme 11-hydroxylase (CYP11B1) and may therefore, owing to the inhibition of cortisol synthesis, be employed for preventing, delaying the progression of or treating Cushing's syndrome and also the physical and mental consequences of excessive and persistent cortisol secretion in states of stress. Consequently, moreover, the compounds can be employed in states such as ectopic ACTH syndrome, the change in adrenocortical mass, primary pigmented nodular adrenocortical disease (PPNAD) and Carney complex (CNC), anorexia nervosa, chronic alcohol poisoning, nicotine or cocaine withdrawal syndrome, post-traumatic stress syndrome, cognitive impairment after a stroke, and cortisol-induced mineralocorticoid excess.

Inhibition of aldosterone synthase (Cyp11B2) and of 11-β-hydroxylase (Cyp11B1) and of aromatase (Cyp19) by compounds described above can be determined by the following in vitro assay:

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have Cyp11A (cholesterol side-chain cleavage), Cyp11B1 (steroid 11β-hydroxylase), Cyp11B2 (aldosterone synthase), Cyp17 (steroid 17α-hydroxylase and/or 17,20-lyase), Cyp19 (aromatase), Cyp21B2 (steroid 21-hydroxylase) and 3β-HSD (hydroxysteroid dehydro-genase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbecco's Modified Eagle'Ham F-12 Medium (DME/F12) which has been supplemented with Ultroser SF Serum (Soprachem, Cergy-Saint-Christophe, France), insulin, transferrin, selenite (I-T-S, Becton Dickinson Biosciences, Franklin Lakes, N.J., USA) and antibiotics in 75 cm² cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum albumin instead of Ultroser SF, for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin II (10 or 100 nanomolar), potassium ions (16 millimolar), forskolin (10 micromolar) or a combination of two stimulants. The excretion of aldosterone, cortisol, corticosterone and estradiol/estrone into the culture medium can be detected and quantified by commercially available, specific monoclonal antibodies in radioimmunoassays in accordance with the manufacturers' instructions. Inhibition of the release of certain steroids can be used as a measure of the respective enzyme inhibition by the added test compounds. The dose-dependent inhibition of enzymic activity by a compound is calculated by means of an inhibition plot which is characterized by an $IC_{50}$.

The $IC_{50}$ values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows:

$$Y=(d-a)/((1+(x/c)^{-b}))+a$$

where:
a=minimum data level
b=gradient
c=$IC_{50}$
d=maximum data level
x=inhibitor concentration.

The compounds of the present invention show inhibitory effects at minimum concentrations of about $10^{-3}$ to about $10^{-10}$ mol/l in the in vitro systems.

The aldosterone-reducing effect of the compounds described herein can be tested in vivo by the following protocol:

Adult male Sprague Dawley rats weighing between 125 and 150 grams are kept, housed individually, under the usual conditions of light and temperature. At 16.00 h on the first day of the experiment, the animals receive a subcutaneous injection of the depot ACTH product in a dose of 1.0 mg/kg of weight (SYNACTEN-Depot, Novartis, Basel, CH). Pilot studies showed that this ACTH dose increased plasma aldosterone and corticosterone significantly by respectively 15-fold and 25-fold over a period of at least 18 hours. At 8.00 h in the morning of the second day, the animals, divided into test groups of 5 animals, receive administration either of water orally or of a compound in a variable dose range of 0.01-10 mg/kg orally by gavage. Two hours later, blood is taken in EDTA-treated Eppendorf vessels. Plasma samples are obtained by centrifugation of the blood and can be stored at −20° C.

An alternative method for stimulating aldosterone synthesis is for adult male, catheterized Wistar rats, weighing between 250 and 350 grams, to be subjected to a low-salt diet for 48 hours and additionally be treated 16 hours, and possibly with additional repetition 2 hours, before the start of the experiment with 10 mg/kg furosemide, administered subcutaneously or intraperitoneally. Pilot studies showed that this pretreatment increases the plasma aldosterone level by 5 to 20-fold over a period of 12-24 hours. The catheters are chronically implanted into the animals' carotid and thus permit periodic blood sampling of a volume of up to 0.2 ml using an AccuSampler (DiLab Europe, Lund, Sweden). The experiment starts with the oral administration of the test substances in a dose range of 0.01-10 mg/kg. The blood samples are taken with the AccuSampler 1 hour before administration of the test substances and subsequently after 2, 4, 6, 8, 12, 16 and 24 hours. The blood samples are anticoagulated with heparin and centrifuged.

The plasma samples of both protocols are tested for the steroid content in precedingly described radioimmunoassays. The reduction in the steroid levels, such as, for example, aldosterone, serves as a measure of the in vivo bioavailability and enzyme inhibition activity of the compounds described herein.

The reduction in damage to the heart through the inhibition of aldosterone synthase with compounds described herein can be shown in vivo by the following protocol. The protocol corresponds in large part to the publication (Rocha et al, Endocrinology, Vol. 141, pp 3871-3878, 2000).

Adult male Wistar rats are housed individually and receive freely available drinking water which contains 0.9% sodium chloride during the experiment. Three days later, the animals are subjected to one of the three following treatments. Group I (control group of 8 animals) is treated for 14 days with the chemical L-NAME (N-nitro-L-arginine methyl ester, Sigma, St. Louis, Mo., USA) which inhibits nitric-oxide synthase. On day 11 of this treatment, an osmotic minipump charged with sodium chloride solution is subcutaneously implanted into each animal. Group II (L-NAME/AngII of 8 animals) is treated with L-NAME for 14 days. On day 11 of this treatment, an osmotic minipump charged with angiotensin II (AngII) solution is subcutaneously implanted into each animal. Group III (L-NAME/AngII/test substance of 8 animals) is treated similarly to group II but receives the test substance in a daily dose range from 0.2 to 10 mg/kg of rat weight. The test substance is for this purpose dissolved in distilled water and administered orally by gavage. Groups I and II receive only the vehicle without test substance. The experiment is stopped on day 14 of L-NAME treatment. L-NAME is administered in a concentration of 60 mg/100 mL in the 0.9% NaCl drinking water, leading to a daily intake of about 60 mg/kg. Angiotensin II is administered by means of an Alzet osmotic minipump (model 2001; Alza Corp, Palo Alto, Calif.). The minipump is implanted subcutaneously in the back of the neck. Angiotensin II (human and with a peptide purity of 99%) is purchased from Sigma Chemical Co., St. Louis, Mo. and administered in a dose of 225 µg/kg/day in sodium chloride solution. The concentration of angiotensin II for charging the pumps is calculated on the basis of: a) the average pumping rate stated by the manufacturer; b) the body weight of the animals on the day before implantation of the pumps; and c) the planned dose.

The rats are sacrificed on day 14. The hearts are removed and the ventricles/atria are sliced like a "loaf of bread" in order to obtain three samples from the following approximate regions of the heart: superior, middle and inferior. The samples are fixed in 10% buffered formalin. Paraffin sections are cut and stained with hematoxylin/eosin. The sections are assessed by a single scientist unaware of the assignment to groups. One section from each region of the heart is analysed for each rat. Specific parts of the heart (left and right ventricle, and the septum) are evaluated separately. The whole section is examined histologically for myocardial damage (irrespective of severity) manifested by myocyte necrosis, inflammatory cells, haemorrhages and general tissue damage. The histological data are assessed on the basis of a comparison of groups II and III, i.e. angiotensin II with and without test substance. Evaluation of the samples can take place semi-quantitatively and be represented in the form of a point table.

The reduction in hypertension and the diminution in damage to the heart and kidneys through inhibition of aldosterone synthase with compounds described herein can be shown in vivo by the following protocol.

The investigations take place in 4-week old, male doubly transgenic rats (dTGR), which overexpress both human angiotensinogen and human renin and consequently develop hypertension. Age-matched Sprague-Dawley (SD) rats serve as non-hypertensive control animals. The animals are divided into treatment groups and receive test substance or vehicle (control) each day for 3-4 weeks. Throughout the study, the animals receive standard feed and tap water ad libitum.

The systolic and diastolic blood pressure, and the heart rate, are measured telemetrically by means of implanted transducers, allowing the animals free and unrestricted movement. The animals are placed once a week in metabolism cages in order to determine the 24-hour urinary excretion of albumin. Heart dimensions (left ventricular mass, end-diastolic diameter and wall thickness, septum thickness, shortening fraction) and diastolic filling are measured by echocardiography at the start and at the end of the treatment under isoflurane anaesthesia (M mode recording in the short axis and tissue Doppler imaging by means of a commercial echocardiography instrument which is equipped with a 15 MHz probe). At the end of the study, the animals are sacrificed and the kidneys and hearts are removed for determining the weight and for immunohistological investigations (fibrosis, macrophage/T cell infiltration, etc.).

In order to achieve the desired effects in a patient to be treated, the compounds of the pre-sent invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatin capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatin, disintegrants such as potato starch or crosslinked polyvinylpyrrolidone (PVPP) and lubricants such as stearic acid or magnesium stearate.

Examples of excipients suitable for soft gelatin capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semi-liquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

as therapeutic combination in the form of a product or of a kit which is composed of individual components consisting of a compound described herein, in free form or as pharmaceutically useful salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.

as method for combined use, such as, for example, in simultaneous or sequential succession, of a therapeutically effective amount of a compound described herein, in free or in pharmaceutically useful salt form, and of a second active ingredient with blood pressure-lowering, inotropic, antidiabetic, obesity-reducing or lipid-lowering effect.

The compounds described herein and their pharmaceutically useful salts can be used in combination with (i) one or more blood pressure-lowering active ingredients, as such for example:
  renin inhibitors such as aliskiren;
  angiotensin II receptor blockers such as candesartan, irbesartan, olmesartan, losartan, valsartan, telmisartan etc.;
  ACE inhibitors such as quinapril, ramipril, trandolapril, lisinopril, captopril, enalapril etc.;
  calcium antagonists such as nifedipine, nicardipine, verapamil, isradipine, nimodipine, amlodipine, felodipine, nisoldipine, diltiazem, fendiline, flunarizine, perhexyline, gallopamil etc.;
  diuretics such as hydrochlorothiazide, chlorothiazide, acetazolamide, amiloride, bumetanide, benzthiazide, etacrynic acid, furosemide, indacrinone, metolazone, triamterene, chlortalidone, etc.;
  aldosterone receptor blockers such as spironolactone, eplerenone;
  endothelin receptor blockers such as bosentan;
  phosphodiesterase inhibitors such as amrinone, sildenafil;
  direct vasodilators such as dihydralazine, minoxidil, pinacidil, diazoxide, nitropnusside, flosequinan etc.,
  α- and β-receptor blockers such as phentolamine, phenoxybenzamine, prazosin, doxazosin, terazosin, carvedilol, atenolol, metoprolol, nadolol, propranolol, timolol, carteolol etc.;
  neutral endopeptidase (NEP) inhibitors;
  sympatholytics such as methyldopa, clonidine, guanabenz, reserpine (ii) one or more agents having inotropic activity, as such for example:
  cardiac glycosides such as digoxin;
  β-receptor stimulators such as dobutamine
  thyroid hormone such as thyroxine (iii) one or more agents having antidiabetic activity, as such for example:
  insulins such as insulin aspart, insulin human, insulin lispro, insulin glargine and further fast-, medium- and long-acting insulin derivatives and combinations
  insulin sensitizers such as rosiglitazone, pioglitazone;
  sulphonylureas such as glimepiride, chlorpropamide, glipizide, glyburide etc.;
  biguanides such as metformin;
  glucosidase inhibitors such as acarbose, miglitol;
  meglitinides such as repaglinide, nateglinide;

(iv) one or more obesity-reducing ingredients, as such for example:
  lipase inhibitors such as orlistat;
  appetite suppressants such as sibutramine, phentermine;

(v) one or more lipid-lowering ingredients, such as, for example,
  HMG-CoA reductase inhibitors such as lovastatin, fluvastatin, pravastatin, atorvastatin, simvastatin, rosuvastatin etc.;
  fibrate derivatives such as fenofibrate, gemfibrozil etc.;
  bile acid-binding active ingredients such as colestipol, colestyramine, colesevelam
  cholesterol absorption inhibitors such as ezetimibe
  nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The compounds described herein and their pharmaceutically useful salts can additionally be used in combination with (i) a diagnostic test system which permits quantitative determination of the plasma aldosterone level (PAC, plasma aldosterone concentration)

(ii) a diagnostic test system which permits quantitative determination of the plasma renin level (PRC, plasma renin concentration)

(iii) a diagnostic test system which permits quantitative determination of the plasma renin activity (PRA, plasma renin activity)

(iv) a diagnostic test system which permits quantitative determination of the plasma aldosterone/renin level (ARC, aldosterone renin concentration)

(v) a diagnostic test system which permits quantitative determination of the plasma aldosterone/renin activity (ARR, aldosterone to renin activity ratio)

(vi) a diagnostic test system which permits quantitative determination of the plasma cortisol level (PCC, plasma cortisol concentration)

Such diagnosis-therapy combinations can be used separately or in products which comprise a plurality of components.

EXAMPLES

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program. Chemical names of spiro-compounds were generated with the aid of the ACD-Name program

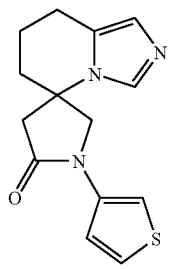

1

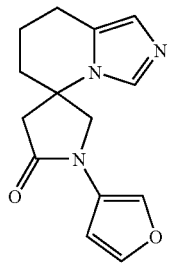

2

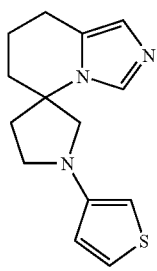

3

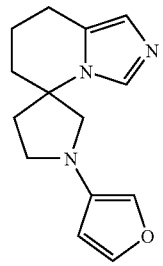

4

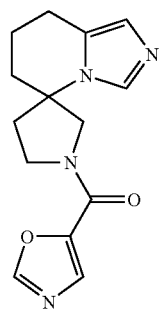

5

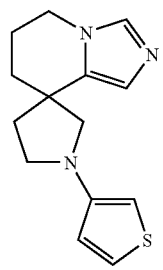

6

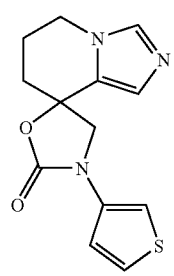

7

Thin-layer chromatography mobile-phase systems:
A Dichloromethane
B Dichloromethane-methanol=99:1
C Dichloromethane-methanol=98:2
D Dichloromethane-methanol=97:3
E Dichloromethane-methanol=96:4
F Dichloromethane-methanol=95:5
G Dichloromethane-methanol=9:1
H Dichloromethane-methanol=4:1
I Dichloromethane-methanol-water-conc. acetic acid=170:26:3:1
J Dichloromethane-methanol-water-conc. acetic acid=150:54:10:1
K Dichloromethane-methanol-conc. ammonia 25%=97:3:1
L Dichloromethane-methanol-conc. ammonia 25%=95:5:1
M Dichloromethane-methanol-conc. ammonia 25%=90:10:1
N Dichloromethane-methanol-conc. ammonia 25%=200:10:1
O Dichloromethane-methanol-conc. ammonia 25%=200:20:1

P Ethyl acetate
Q Ethyl acetate-heptane=3:1
R Ethyl acetate-heptane=2:1
S Ethyl acetate-heptane=1:1
T Ethyl acetate-heptane=1:2
U Ethyl acetate-heptane=1:3
V Ethyl acetate-heptane=1:4
W Ethyl acetate-heptane=1:5
X Ethyl acetate-heptane=1:6
Y Ethyl acetate-heptane=1:10
Z Toluene/ethyl acetate=1:1
AA Toluene/methanol=6:1
HPLC gradients on Hypersil BDS C-18 (5 µm); column: 4×125 mm:
95% water*/5% acetonitrile* to 0% water*/100% acetonitrile* in 10 minutes+2 minutes (1 ml/min)
* contains 0.1% trifluoroacetic acid
The abbreviations used are as follows:
Rf ratio of distance traveled by a substance to distance of the eluent from the starting point in thin-layer chromatography
Rt retention time of a substance in HPLC (in minutes)
m.p. melting point (temperature)

Example 1

1'-(3-Thienyl)-7,8-dihydro-5'H,6H-spiro[imidazo[1,5-a]pyridine-5,3'-pyrrolidin]-5'-one A mixture consisting of 0.1 mmol of copper(I) iodide and 4.3 mmol of potassium carbonate is admixed with 3 ml of 1,4-dioxane, 0.1 mmol of racemic trans-N,N-dimethylcyclohexanediamine, 1.0 mmol of 3-bromothiophen [872-31-1] and 1.0 mmol of 7,8-dihydro-5'H,6H-spiro[imidazo[1,5-a]pyridine-5,3'-pyrrolidin]-5'-one. The reaction mixture is heated at 110° C. for 24 hours, cooled to room temperature and concentrated. From the residue the title compound is identified by means of flash chromatography (SiO$_2$ 60 F) on the basis of the Rf value.

The starting material is prepared as follows:

a) 7,8-Dihydro-5'H,6H-spiro[imidazo[1,5-a]pyridine-5,3'-pyrrolidin]-5'-one

A mixture of 1.9 mmol 6,7,8,8a-tetrahydro-1H,5'H-spiro[imidazo[1,5-a]pyridine-5,3'-pyrrolidin]-5'-one and 3 g of manganese dioxide in 50 ml of toluene is heated at reflux for 1.5 hours. The reaction mixture is cooled to room temperature, the solid is isolated by filtration over Hyflo and the filtrate is evaporated. From the residue the title compound is obtained by means of flash chromatography (SiO$_2$ 60 F) and identified on the basis of the Rf value.

b) 6.7.8.8a-Tetrahydro-1H,5'H-spiro[imidazo[1,5-a]pyridine-5,3'-pyrrolidin]-5'-one A solution of 31 mmol of 7-aminomethyl-2,6-diazspiro[4,5]decan-3-one and 31 mmol of N,N-dimethylformamide dimethyl acetal in 50 ml of dichloromethane is heated at reflux for 6 hours. The reaction mixture is cooled to room temperature and evaporated. From the residue the crude title compound is identified on the basis of the Rf value. The title compound is used without further purification in the next stage.

c) 7-Aminomethyl-2,6-diazaspiro[4,5]decan-3-one

A suspension of 5.590 mmol of (2,6-bis-aminomethylpiperidin-2-yl)acetic acid hydrochloride and 22.340 mmol of N-ethyldiisopropylamine in 20 ml of ethyl acetate is admixed dropwise at 0° C. with a solution of 11.170 mmol of propylphosphonic anhydride (T3P®) (50% w/w in ethyl acetate). The reaction mixture is subsequently stirred at room temperature for 20 h. It is admixed with water (20 ml) the organic phase is separated off and the aqueous phase is extracted with ethyl acetate (3×). The combined organic phases are dried over sodium sulphate and evaporated. From the residue the title compound is obtained by means of flash chromatography (SiO$_2$ 60 F) and identified on the basis of the Rf value.

d) (2,6-bis-Aminomethylpiperidin-2-yl)acetic acid hydrochloride

A solution of 6.00 mmol of tert-butyl (1-benzyl-2,6-dicyanopiperidin-2-yl)acetate in 40 ml of methanol is admixed with 2 ml of 37% strength aqueous hydrochloric acid and 0.600 g of 10% Pd/C. The reaction mixture is hydrogenated with 4 bar of hydrogen at 22° C. for 18 hours. The reaction mixture is filtered over Hyflo and the filtrate is evaporated. From the residue the crude title compound is identified on the basis of the Rf value. The title compound is used without further purification in the next stage.

e) tert-Butyl (1-benzyl-2,6-dicyanopiperidin-2-yl)acetate

A solution of 378.000 mmol of diisopropylamine in 180 ml of tetrahydrofuran is admixed dropwise at −78° C. with 179.000 mmol of n-butyllithium (1.6M in hexane). The yellowish solution is stirred at −20° C. for 30 minutes then cooled again to −78° C. This solution is admixed dropwise at −78° C. with a solution of 126.000 mmol of 1-benzylpiperidine-2,6-dicarbonitrile [98195-08-5] and 138.600 mmol of hexamethylphosphorictriamide in 50 ml of tetrahydrofuran. The mixture is subsequently stirred at this temperature for 30 minutes. Then a solution of 130.000 mmol of tert-butyl bromoacetate in 50 ml of tetrahydrofuran is added dropwise. The mixture is subsequently stirred at −78° C. for an hour, the cold bath is removed, and the temperature is allowed to increase slowly overnight to room temperature. The reaction mixture is admixed with aqueous saturated ammonium chloride solution, the organic phase is separated off and the aqueous phase is extracted repeatedly with diethyl ether. The combined organic phases are washed with water and brine, dried with sodium sulphate and evaporated. From the residue the title compound is obtained by means of flash chromatography (SiO$_2$ 60 F) and identified on the basis of the Rf value.

In accordance with the method described in Example 1 the following compound is prepared analogously:
2  1'-(3-Furyl)-7,8-dihydro-5'H,6H-spiro[imidazo[1,5-a]pyridine-5,3'-pyrrolidin]-5'-one starting from 7,8-dihydro-5'H,6H-spiro[imidazo[1,5-a]pyridine-5,3'-pyrrolidin]-5'-one (Example 1a)

Example 3

1'-(3-Thienyl)-7,8-dihydro-6H-spiro[imidazo[1,5-a]pyridine-5,3'-pyrrolidine]

A solution of 1.0 mmol of 1'-(3-thienyl)-7,8-dihydro-5'H,6H-spiro[imidazo[1,5-a]pyridine-5,3'-pyrrolidin]-5'-one (Example 1) in 10 ml of tetrahydrofuran is admixed with 3.0 mmol of a solution of borane-tetrahydrofuran complex (1M in tetrahydrofuran). The reaction mixture is heated to 50° C. and stirred overnight. It is allowed to cool to room temperature and then cautiously admixed with 10 ml of methanol.

When evolution of gas is at an end, the reaction mixture is concentrated. From the residue the title compound is identified by means of flash chromatography (SiO$_2$ 60 F) on the basis of the Rf value.

Alternative synthesis for 1'-(3-thienyl)-7,8-dihydro-6H-spiro[imidazo[1,5-a]pyridine-5,3'-pyrrolidine]:

1'-(3-Thienyl)-7,8-dihydro-6H-spiro[imidazo[1,5-a]pyridine-5,3'-pyrrolidine]

A solution of 1.0 mmol of 7,8-dihydro-6H-spiro[imidazo[1,5-a]pyridine-5,3'-pyrrolidine] in 10 ml of toluene is admixed with 2.0 mmol of 3-bromothiophene, 3.0 mmol of sodium tert-butoxide, 0.05 mmol of palladium bis(dibenzylideneacetone) and 0.05 mmol of tris-tert-butylphosphine. The resulting suspension is heated at 100° C. for 24 hours. After the end of reaction the mixture is concentrated and from the residue the title compound is identified by means of flash chromatography (SiO$_2$ 60 F) on the basis of the Rf value.

The starting material is prepared as follows:

a) 7,8-Dihydro-6H-spiro[imidazo[1,5-a]pyridine-5,3'-pyrrolidine]

A solution of 1.0 mmol of 7,8-dihydro-5'H,6H-spiro[imidazo[1,5-a]pyridine-5,3'-pyrrolidin]-5'-one (Example 1a) in 10 ml of tetrahydrofuran is admixed with 3.0 mmol of a solution of borane-tetrahydrofuran complex (1M in tetrahydrofuran). The reaction mixture is heated to 50° C. and stirred overnight. It is allowed to cool to room temperature and then cautiously admixed with 10 ml of methanol. When evolution of gas is at an end, the reaction mixture is concentrated. From the residue the title compound is identified by means of flash chromatography (SiO$_2$ 60 F) on the basis of the Rf value.

In accordance with the method described in Example 3 the following compound is prepared analogously:

4 1'-(3-Furyl)-7,8-dihydro-6H-spiro[imidazo[1,5-a]pyridine-5,3'-pyrrolidine]l starting from 1'-(3-furyl)-7,8-dihydro-5'H,6H-spiro[imidazo[1,5-a]pyridine-5,3'-pyrrolidin]-5'-one (Example 2)

Example 5

1'-(1,3-Oxazol-5-ylcarbonyl)-7,8-dihydro-6H-spiro[imidazo[1,5-a]pyridine-5,3'-pyrrolidine]

1.5 mmol of oxazole-5-carboxylic acid [118994-90-4] are dissolved in 5 ml of dichloro-methane and the solution is admixed at 0° C. with 1.6 mmol of chlorenamine. The reaction solution is subsequently stirred at room temperature for an hour and then added dropwise at 0° C. to a solution of 1 mmol of 7,8-dihydro-6H-spiro[imidazo[1,5-a]pyridine-5,3'-pyrrolidine] (Example 3a) and 2 mmol of triethylamine in 5 ml of dichloromethane. The reaction mixture is subsequently stirred at room temperature for 3 hours, poured into saturated aqueous sodium hydrogen carbonate solution and extracted with dichloromethane (3×). The combined organic extracts are washed with brine, dried with sodium sulphate and evaporated. From the residue the title compound is identified by means of flash chromatography (SiO$_2$ 60 F) on the basis of the Rf value.

Example 6

1'-(3-Thienyl)-6,7-dihydro-5H-spiro[imidazo[1,5-a]pyridine-8,3'-pyrrolidine]

A solution of 1.0 mmol of 6,7-dihydro-5H-spiro[imidazo[1,5-a]pyridine-8,3'-pyrrolidine] in 10 ml of toluene is admixed with 2.0 mmol of 3-bromothiophene, 3.0 mmol of sodium tert-butoxide, 0.05 mmol of palladium bis(dibenzylideneacetone) and 0.05 mmol of tris-tert-butylphosphine. The resulting suspension is heated at 100° C. for 24 hours. After the end of reaction the mixture is concentrated and from the residue the title compound is identified by means of flash chromatography (SiO$_2$ 60 F) on the basis of the Rf value.

The starting materials are prepared as follows:

a) 6,7-Dihydro-5H-spiro[imidazo[1,5-a]pyridine-8,3'-pyrrolidine]

A solution of 1.00 mmol of 1'-benzyl-6,7-dihydro-5H-spiro[imidazo[1,5-a]pyridine-8,3'-pyrrolidine] in 5 ml of methanol is admixed with 1 mmol of 2M aqueous hydrochloric acid and 0.10 g of 10% Pd/C. The reaction mixture is hydrogenated with 1 bar of hydrogen at 22° C. for 18 hours. The reaction mixture is filtered over Hyflo and the filtrate is evaporated. The residue is taken up in ethyl acetate and the amine is liberated with saturated aqueous sodium carbonate solution. The phases are separated and the aqueous phase is extracted with ethyl acetate. The combined organic phases are dried with sodium sulphate and evaporated. From the residue the title compound is identified by means of flash chromatography (SiO$_2$ 60 F) on the basis of the Rf value.

b) 1'-Benzyl-6,7-dihydro-5H-spiro[imidazo[1,5-a]pyridine-8,3'-pyrrolidine]

The title compound is obtained by a method analogous to that described in Example 1a and 1b, starting from C-(2-benzyl-2,7-diazaspiro[4.5]dec-6-yl)methylamine, and identified on the basis of the Rf value.

c) C-(2-benzyl-2,7-diazaspiro[4.5]dec-6-yl)methylamine 1 mmol of tert-butyl 6-aminomethyl-2-benzyl-2,7-diazaspiro[4.5]decane-7-carboxylate is dissolved in 2 ml of dichloromethane and the solution is admixed with 2 ml of trifluoroacetic acid. The reaction solution is stirred at room temperature until conversion is complete and then is poured into saturated aqueous sodium hydrogen carbonate solution. The phases are separated and the aqueous phase is extracted with dichloromethane. The combined organic phases are washed with brine, dried over sodium sulphate and evaporated. From the residue the title compound is identified by means of flash chromatography (SiO$_2$ 60 F) on the basis of the Rf value.

d) tert-Butyl 6-aminomethyl-2-benzyl-2,7-diazaspiro[4.5]decane-7-carboxylate 1 mmol of tert-butyl 6-azido-2-benzyl-2,7-diazaspiro[4.5]decane-7-carboxylate is dissolved in 5 ml of tetrahydrofuran. The solution is admixed with 1.5 mmol of triphenylphosphine and a few drops of 25% ammonium hydroxide solution and stirred at room temperature for 18 hours. The reaction solution is evaporated and from the residue the title compound is identified by means of flash chromatography (SiO$_2$ 60 F) on the basis of the Rf value.

e) tert-Butyl 6-azido-2-benzyl-2,7-diazaspiro[4.5]decane-7-carboxylate 10 mmol of tert-butyl 2-benzyl-6-methanesulphonyloxymethyl-2,7-diazaspiro[4.5]decane-7-carboxylate are dissolved in 20 ml of N,N-dimethylformamide and the solution is admixed with 15 mmol of sodium azide. The reaction mixture is heated at 60° C. for 6 hours, then poured into water and extracted with tert-butyl methyl ether. The combined organic extracts are washed with brine, dried with sodium sulphate and evaporated. From the residue the title compound is identified by means of flash chromatography ($SiO_2$ 60 F) on the basis of the Rf value.

f) tert-Butyl 2-benzyl-6-methanesulphonyloxymethyl-2,7-diazaspiro[4.5]decane-7-carboxylate A solution of 10 mmol of tert-butyl 2-benzyl-6-hydroxymethyl-2,7-diazaspiro[4.5]decane-7-carboxylate in 30 ml of dichloromethane is admixed at 0° C. with 15 mmol of triethylamine, followed by 11 mmol of methanesulphonyl chloride. The reaction mixture is stirred at 0° C. for an hour and then at room temperature for an hour. The reaction mixture is poured into saturated aqueous sodium hydrogen carbonate solution and extracted with dichloromethane. The combined organic extracts are washed with brine, dried with sodium sulphate and evaporated. From the residue the title compound is identified by means of flash chromatography ($SiO_2$ 60 F) on the basis of the Rf value.

g) tert-Butyl 2-benzyl-6-hydroxymethyl-2,7-diazaspiro[4.5]decane-7-carboxylate

A solution of 5 mmol of tert-butyl 2-benzyl-6-methylene-2,7-diazaspiro[4.5]decane-7-carboxylate in 60 ml of tetrahydrofuran is admixed at 0° C. with 10.6 mmol of 9-borabicyclo[3.3.1]nonane (0.5M in tetrahydrofuran). The reaction solution is stirred at 60° C. for 15 hours and then cooled to room temperature. The solution is admixed with 50 ml each of 3M sodium hydroxide solution and 30% hydrogen peroxide. The reaction mixture is stirred at room temperature for 2 hours. Subsequently the phases are separated and the aqueous phase is saturated with potassium carbonate and extracted with ethyl acetate (3×). The combined organic phases are dried over sodium sulphate and evaporated. From the residue the title compound is identified by means of flash chromatography ($SiO_2$ 60 F) on the basis of the Rf value.

h) tert-Butyl 2-benzyl-6-methylene-2,7-diazaspiro[4,5]decane-7-carboxylate 8.7 mmol of tert-butyl 2-benzyl-6-oxo-2,7-diazaspiro[4.5]decane-7-carboxylate are dissolved in a mixture of 75 ml of toluene and 0.75 ml of pyridine. The solution is admixed with 10.0 mmol of bis(cyclopentadienyl)dimethyltitanium [1271-66-5] and heated at 70° C. for 20 hours. The reaction solution is evaporated and the residue is taken up in pentane. The mixture is filtered over Hyflo and the filtrate is evaporated. From the residue the title compound is identified by means of flash chromatography ($SiO_2$ 60 F) on the basis of the Rf value.

i) tert-Butyl 2-benzyl-6-oxo-2,7-diazaspiro[4.5]decane-7-carboxylate

A solution of 1 mmol of 2-benzyl-2,7-diaza-spiro[4.5]decan-6-one in 5 ml of acetonitrile is treated with 2.2 mmol of N,N-dimethylaminopyridine and 2.2 mmol of di-tert-butyl dicarbonate. The reaction mixture is stirred for 48 hours at room temperature, then poured into water and extracted with tert-butyl methyl ether (3×). The combined organic phases are washed with brine, dried with sodium sulphate and evaporated. From the residue the title compound is identified by means of flash chromatography ($SiO_2$ 60 F) on the basis of the Rf value.

j) 2-Benzyl-2,7-diaza-spiro[4.5]decan-6-one

A solution of 1 mmol of methanesulphonic acid 3-(2-methanesulphonyloxy-ethyl)-2-oxo-piperidin-3-ylmethyl ester and 3 mmol of benzylamine in 5 ml of dioxane is heated at 60° C. for 30 hours. The reaction mixture is diluted with tert-butyl methyl ether and washed with brine. The organic phase is dried with sodium sulphate and evaporated. From the residue the title compound is identified by means of flash chromatography ($SiO_2$ 60 F) on the basis of the Rf value.

k) Methanesulphonic acid 3-(2-methanesulphonyloxy-ethyl)-2-oxo-piperidin-3-ylmethyl ester A solution of 1 mmol of 3-(2-hydroxy-ethyl)-3-hydroxymethyl-piperidin-2-one in 3 ml of dichloromethane is admixed at 0° C. with 3 mmol of triethylamine, followed by 2.2 mmol of methanesulphonyl chloride. The reaction mixture is stirred at 0° C. for an hour and then at room temperature for an hour. The reaction mixture is poured into saturated aqueous sodium hydrogen carbonate solution and extracted with dichloromethane (2×). The combined organic extracts are washed with brine, dried with sodium sulphate and evaporated. From the residue the title compound is identified by means of flash chromatography ($SiO_2$ 60 F) on the basis of the Rf value.

l) 3-(2-Hydroxy-ethyl)-3-hydroxymethyl-piperidin-2-one

A solution of 1 mmol of 3-ethoxycarbonylmethyl-2-oxo-piperidine-3-carboxylic acid ethyl ester, 1 mmol of calcium chloride, and 5 ml of methanol is cooled to 0° C. and treated with one portion of 1 mmol of sodium borohydride, keeping the temperature at 0-5° C. with cooling for 2 hours. The mixture is allowed to warm to room temperature overnight. The solids are filtered and washed with methanol. The methanol filtrate is concentrated. The residue is triturated with diethyl ether and decanted. The residue is treated with water and the separated solid is filtered and washed with water. The aqueous filtrates are saturated with potassium carbonate and extracted with dichloromethane (3×) methylene chloride. The combined organic extracts and are dried over potassium carbonate, filtered, and concentrated. From the residue the crude title compound is identified on the basis of the Rf value. The title compound is used without further purification in the next stage.

l) 3-Ethoxycarbonylmethyl-2-oxo-piperidine-3-carboxylic acid ethyl ester

To a stirred solution of 5 mmol of 2-oxo-piperidine-3-carboxylic acid ethyl ester [3731-16-6] in 30 ml dry of tetrahydrofuran is added dropwise 5.25 mmol of an n-butyl lithium solution (1.6M in hexane) at −78° C. After stirring for 15 minutes at −78° C., trimethylsilyl chloride (0.67 mL, 5.25 mmol) is added dropwise and stirring is continued for 30 minutes while the solution is allowed to warm to 0° C. The reaction mixture is then cooled to −78° C. and transferred (via cannula) to a solution of 5 mmol of freshly prepared lithium diisopropyl-amide in 20 ml of dry tetrahydrofuran at −78° C. After stirring for 30 minutes at −78° C., 5.25 mmol of 2-bromoacetic acid ethyl ester [105-36-2] are added drop wise and stirring is continued for 1 hour while the solution is allowed to warm to 0° C. The reaction is quenched by addition of aqueous saturated ammonium chloride solution and extracted with diethyl ether (3×). The combined organic phases are washed with brine, dried with sodium sulphate and evaporated. From the residue the title compound is identified by means of flash chromatography (SiO$_2$ 60 F) on the basis of the Rf value.

Example 7

3'-(3-Thienyl)-6,7-dihydro-2'H,5H-spiro[imidazo[1,5-a]pyridine-8,5'-[1,3]oxazolidin]-2'-one The title compound is obtained by a method analogous to that described in Example 1, starting from 6,7-dihydro-2'H,5H-spiro[imidazo[1,5-a]pyridine-8,5'-[1,3]oxazolidin]-2'-one, and identified on the basis of the Rf value.
The starting materials are prepared as follows:

a) 6,7-Dihydro-2'H,5H-spiro[imidazo[1,5-a]pyridine-8,5'-[1,3]oxazolidin]-2'-one

A solution of 1.00 mmol of 8-aminomethyl-5,6,7,8-tetrahydroimidazo[1,5-a]pyridin-8-ol in 5 ml of tetrahydrofuran is admixed with 1.00 mmol of N,N'-carbonyldiimidazole. The reaction solution is heated at reflux for 15 hours and then evaporated. From the residue the title compound is obtained by means of flash chromatography (SiO$_2$ 60 F) and identified on the basis of the Rf value.

b) 8-Aminomethyl-5,6,7,8-tetrahydroimidazo[1,5-a]pyridin-8-ol 3 mmol of 8-azidomethyl-5,6,7,8-tetrahydroimidazo[1,5-a]pyridin-8-ol are taken up in 10 ml of methanol and the solution is admixed with 0.30 mmol of 10% Pd/C. The reaction mixture is hydrogenated with a hydrogen pressure of 1 bar at 22° C. for 1-10 hours. The catalyst is filtered off over Hyflo and the filtrate is evaporated. From the residue the title compound is identified by means of flash chromatography (SiO$_2$ 60 F) on the basis of the Rf value.

c) 8-Azidomethyl-5,6,7,8-tetrahydroimidazo[1,5-a]pyridin-8-ol

A solution of 5 mmol of 6,7-dihydro-5H-spiro[imidazo[1,5-a]pyridine-8,2'-oxirane] in 15 ml of N,N-dimethylformamide is admixed with 10 mmol of sodium azide and the reaction mixture is heated at 60° C. for 4 hours. The mixture is poured into water and extracted with tert-butyl methyl ether. The combined organic extracts are washed with brine, dried with sodium sulphate and evaporated. From the residue the title compound is identified by means of flash chromatography (SiO$_2$ 60 F) on the basis of the Rf value.

d) 6,7-Dihydro-5H-spiro[imidazo[1,5-a]pyridine-8,2'-oxirane]

Sodium hydride (22 mmol) washed with pentane is admixed under argon with 20 ml of dimethyl sulphoxide. The mixture is heated at 60° C. for an hour and then diluted with 5 ml of tetrahydrofuran. The mixture is cooled to 0° C. and a solution of 21 mmol of trimethyl-sulphonium iodide in 5 ml of N,N-dimethylformamide is added at 0° C., after which the mixture is stirred for 10 minutes. A solution of 20 mmol of 6,7-dihydro-5H-imidazo[1,5-a]pyridin-8-one [426219-51-4] in 5 ml of N,N-dimethylformamide is added and the reaction mixture is stirred at 60° C. for 18 hours. The reaction mixture is poured into cold brine and extracted with tert-butyl methyl ether. The combined organic phases are washed with brine, dried with sodium sulphate and evaporated. From the residue the title compound is identified by means of flash chromatography (SiO$_2$ 60 F) on the basis of the Rf value.

The invention claimed is:
1. A compound of the formula (Ia') or (Ib')

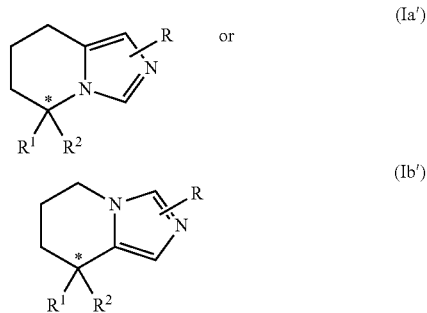

in which
R is hydrogen, $C_1$-$C_8$-alkyl, $C_1$-$C_8$-alkoxy-$C_0$-$C_4$-alkyl, halogen, tri-$C_1$-$C_4$-alkylsilyl, deuterium or trifluoromethyl;
$R^1$ together with $R^2$ is a ring selected from the group consisting of

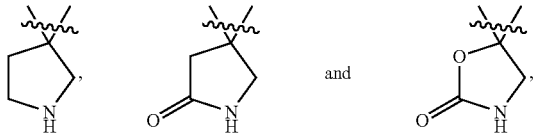

which rings may be substituted by 1-4 members selected from the group consisting of oxo, cyano-$C_0$-$C_6$-alkyl, $C_0$-$C_8$-alkylcarbonyl, thiophene, furan, oxazole, thiophenylcarbonyl, furanylcarbonyl and oxazolylcarbonyl, it being possible for thiophene, furan, oxazole, thiophenylcarbonyl, furanylcarbonyl and oxazolylcarbonyl to be unsubstituted or substituted by 1-4 members selected from the group consisting of $C_1$-$C_8$-alkyl, halogen, cyano and $C_0$-$C_8$-alkylcarbonyl; and
"*" denotes an asymmetric carbon atom;
or a pharmaceutically acceptable salt thereof.
2. A compound according to claim 1, wherein R is hydrogen or deuterium.
3. A compound according to claim 1, wherein $R^1$ together with $R^2$ is a ring selected from the group consisting of

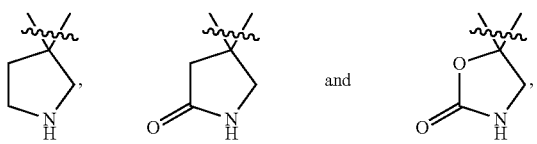

which rings may be substituted by thiophene, furan, oxazole, thiophenylcarbonyl, furanylcarbonyl or oxazolylcarbonyl, it being possible for thiophene, furan, oxazole, thiophenylcarbonyl, furanylcarbonyl and oxazolylcarbonyl to be unsubstituted or substituted by 1-4 members selected from the group consisting of $C_1$-$C_8$-alkyl, halogen and cyano.

4. A compound according to claim 1, wherein $R^1$ together with $R^2$ is ring selected from the group consisting of

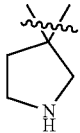 and 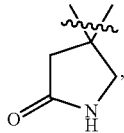, which rings may be substituted by thiophene, furan, oxazole, thiophenylcarbonyl, furanylcarbonyl or oxazolylcarbonyl, it being possible for thiophene, furan, oxazole, thiophenylcarbonyl, furanylcarbonyl and oxazolylcarbonyl to be unsubstituted or substituted by 1-4 members selected from the group consisting of $C_1$-$C_8$-alkyl, halogen and cyano.

5. A compound according to claim 1, wherein
R is hydrogen or deuterium; and
$R^1$ together with $R^2$ is a ring selected from the group consisting of

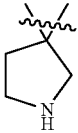 and 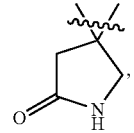, which rings may be substituted by thiophene, furan, oxazole or oxazolylcarbonyl, it being possible for thiophene, furan, oxazole and oxazolylcarbonyl to be unsubstituted or substituted by 1-4 members selected from the group consisting of $C_1$-$C_8$-alkyl, halogen and cyano.

6. A pharmaceutical composition comprising a compound of the formula (Ia') or (Ib') according to claim 1 and conventional excipients.

* * * * *